(12) United States Patent
Zenati et al.

(10) Patent No.: US 7,527,634 B2
(45) Date of Patent: May 5, 2009

(54) DEVICE AND METHOD OF USE FOR FUNCTIONAL ISOLATION OF ANIMAL OR HUMAN TISSUES

(75) Inventors: Marco Zenati, Pittsburgh, PA (US); David S. Schwartzman, Pittsburgh, PA (US); Mark J. Gartner, Wexford, PA (US); Daniel T. McKeel, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 646 days.

(21) Appl. No.: 10/439,280

(22) Filed: May 14, 2003

(65) Prior Publication Data
US 2004/0030335 A1 Feb. 12, 2004

Related U.S. Application Data

(60) Provisional application No. 60/380,630, filed on May 14, 2002.

(51) Int. Cl.
*A61B 17/08* (2006.01)
*A61B 17/24* (2006.01)
*A61B 17/22* (2006.01)
*A61B 1/00* (2006.01)

(52) U.S. Cl. .................. 606/151; 606/115; 606/127; 600/129

(58) Field of Classification Search .................. 606/151, 606/113–115, 127; 600/127, 129
See application file for complete search history.

(56) References Cited

U.S. PATENT DOCUMENTS

| 4,654,594 | A | 3/1987 | Sepponen |
| 4,769,620 | A | 9/1988 | Nicotra |
| 5,007,426 | A | 4/1991 | Le Roux |
| 5,108,420 | A | 4/1992 | Marks |
| 5,190,541 | A | 3/1993 | Abele et al. |
| 5,282,844 | A | 2/1994 | Stokes et al. |
| 5,306,234 | A | 4/1994 | Johnson |
| 5,403,311 | A | 4/1995 | Abele et al. |
| 5,423,830 | A * | 6/1995 | Schneebaum et al. ....... 606/115 |
| 5,643,255 | A | 7/1997 | Organ |
| 5,709,224 | A | 1/1998 | Behl et al. |
| 5,727,569 | A | 3/1998 | Benetti et al. |
| 5,735,848 | A | 4/1998 | Yates et al. |

(Continued)

FOREIGN PATENT DOCUMENTS

WO    WO 2006/110734    10/2006

OTHER PUBLICATIONS

Ernst, G., et al., *Morphology of the Left Atrial Appendate*, The Anatomical Record, 242:553-561, 1995.

(Continued)

*Primary Examiner*—Katherine M Dowe
(74) *Attorney, Agent, or Firm*—Reed Smith LLP

(57) ABSTRACT

A method and apparatus for functionally occluding the lumen of the left atrial appendage (LAA) is provided. Access to the LAA is through an epicardial approach. The devices function to capture the LAA through various non-invasive means. After capturing the LAA with the devices and methods provided, a clamping device is preferably disposed about the base of the appendage. In certain embodiments, the appendage remains viable subsequent to the functional occlusion of the lumen.

11 Claims, 15 Drawing Sheets

U.S. PATENT DOCUMENTS

| | | | |
|---|---|---|---|
| 5,814,052 A * | 9/1998 | Nakao et al. | 606/115 |
| 5,843,152 A | 12/1998 | Tu et al. | |
| 5,865,791 A * | 2/1999 | Whayne et al. | 604/500 |
| 5,897,487 A * | 4/1999 | Ouchi | 600/127 |
| 5,906,620 A * | 5/1999 | Nakao et al. | 606/113 |
| 5,984,917 A | 11/1999 | Fleischman et al. | |
| 6,016,452 A | 1/2000 | Kasevich | |
| 6,019,722 A | 2/2000 | Spence et al. | |
| 6,077,261 A | 6/2000 | Behl et al. | |
| 6,080,173 A | 6/2000 | Williamson, IV et al. | |
| 6,152,144 A | 11/2000 | Lesh et al. | |
| 6,203,541 B1 | 3/2001 | Keppel | |
| 6,231,561 B1 | 5/2001 | Frazier et al. | |
| 6,241,727 B1 | 6/2001 | Tu et al. | |
| 6,248,124 B1 | 6/2001 | Pedros et al. | |
| 6,277,065 B1 | 8/2001 | Donofrio | |
| 6,280,415 B1 | 8/2001 | Johnson | |
| 6,290,674 B1 | 9/2001 | Roue et al. | |
| 6,299,612 B1 | 10/2001 | Ouchi | |
| 6,315,715 B1 | 11/2001 | Taylor et al. | |
| 6,322,494 B1 | 11/2001 | Bullivant et al. | |
| 6,328,688 B1 | 12/2001 | Borst et al. | |
| 6,334,843 B1 | 1/2002 | Borst et al. | |
| 6,336,898 B1 | 1/2002 | Borst et al. | |
| 6,340,344 B1 | 1/2002 | Christopher | |
| 6,357,100 B2 | 3/2002 | Speller, Jr. et al. | |
| 6,416,554 B1 | 7/2002 | Alferness et al. | |
| 6,485,407 B2 * | 11/2002 | Alferness et al. | 600/37 |
| 6,488,689 B1 | 12/2002 | Kaplan et al. | |
| 6,491,706 B1 | 12/2002 | Alferness et al. | |
| 6,494,211 B1 | 12/2002 | Boyd et al. | |
| 6,506,149 B2 | 1/2003 | Peng et al. | |
| 6,506,166 B1 * | 1/2003 | Hendler et al. | 600/562 |
| 6,514,250 B1 | 2/2003 | Jahns et al. | |
| 6,666,861 B1 * | 12/2003 | Grabek | 606/41 |
| 2001/0039419 A1 | 11/2001 | Franchischelli et al. | |
| 2001/0039434 A1 | 11/2001 | Frazier et al. | |
| 2001/0039435 A1 | 11/2001 | Roue et al. | |
| 2002/0002372 A1 | 1/2002 | Jahns et al. | |
| 2002/0022860 A1 | 2/2002 | Borillo et al. | |
| 2002/0035374 A1 | 3/2002 | Borillo et al. | |
| 2002/0049457 A1 | 4/2002 | Kaplan et al. | |
| 2002/0099390 A1 * | 7/2002 | Kaplan et al. | 606/139 |
| 2002/0103492 A1 | 8/2002 | Kaplan et al. | |
| 2002/0111637 A1 | 8/2002 | Kaplan et al. | |
| 2002/0143326 A1 | 10/2002 | Foley et al. | |
| 2003/0023266 A1 | 1/2003 | Borillo et al. | |
| 2003/0032952 A1 | 2/2003 | Hooven | |
| 2003/0191459 A1 * | 10/2003 | Ganz et al. | 606/15 |
| 2007/0073313 A1 | 3/2007 | Liddicoat et al. | |

OTHER PUBLICATIONS

Johnson, W. Dudley, et al., *The Left Atrial Appendate: Our Most Lethal Human Attachment! Surgical Implications*, European Journal of Cardio- Thoracic Surgery 17, 718-722, 2002.

Sperli, Aymar E., MD, *Electrosurgical Peeling (Radiofrequency Resurfacing)*; International Journal of Plastic & Aesthetic Surgery, 1-8, 2002.

Sievert, H., et al., *Percutaneous Left Atrial Appendate Transcatheter Occlusion to Prevent Stroke in High-Risk Patients With Atrial Fibrillation, Early Clinical Experience*, 105:1887-1889, 2002.

Thompson, R., et al., *TissueLink SF30™ Sealing Forceps in Thoracic Surgery Radio Frequency Coupled with Conductive Fluid for Hemostasis and Aerostasis*, TissueLink Medical, Inc., 2002.

Al-Saady, N. M., et al., *Left Atrial Appendate: Structure, Function, and Role in Thromboembolism*, Heart, 82:547-555, 1999.

Blackshear JL, Odell JA., *Appendage obliteration to reduce stroke in cardiac surgical patients with atrial fibrillation*. Ann Thorac. Surg., 1996.61(2):755-9.

Lindsay BD., *Obliteration of the left atrial appendage: A concept worth testing*. Ann Thorac. Surg., 1996.61(2):515.

Schmidt, H., *Prevalence of left atrial chamber and appendage thrombi in patients with atrial flutter and its clinical significance*; J. Am. Coll. Cardiol. 38: 785-88, 2001.

Rosenzweig, B.P., *Thromboembolus from a ligated left atrial appendage*. J. Am. Soc. Echocardiogr. 14: 396-98, 2001.

Jaber, W. A., *Efficacy of anticoagulation in resolving left atrial and left atrial appendage thrombi*; Am. Heart J. 140: 150-56, 2000.

\* cited by examiner

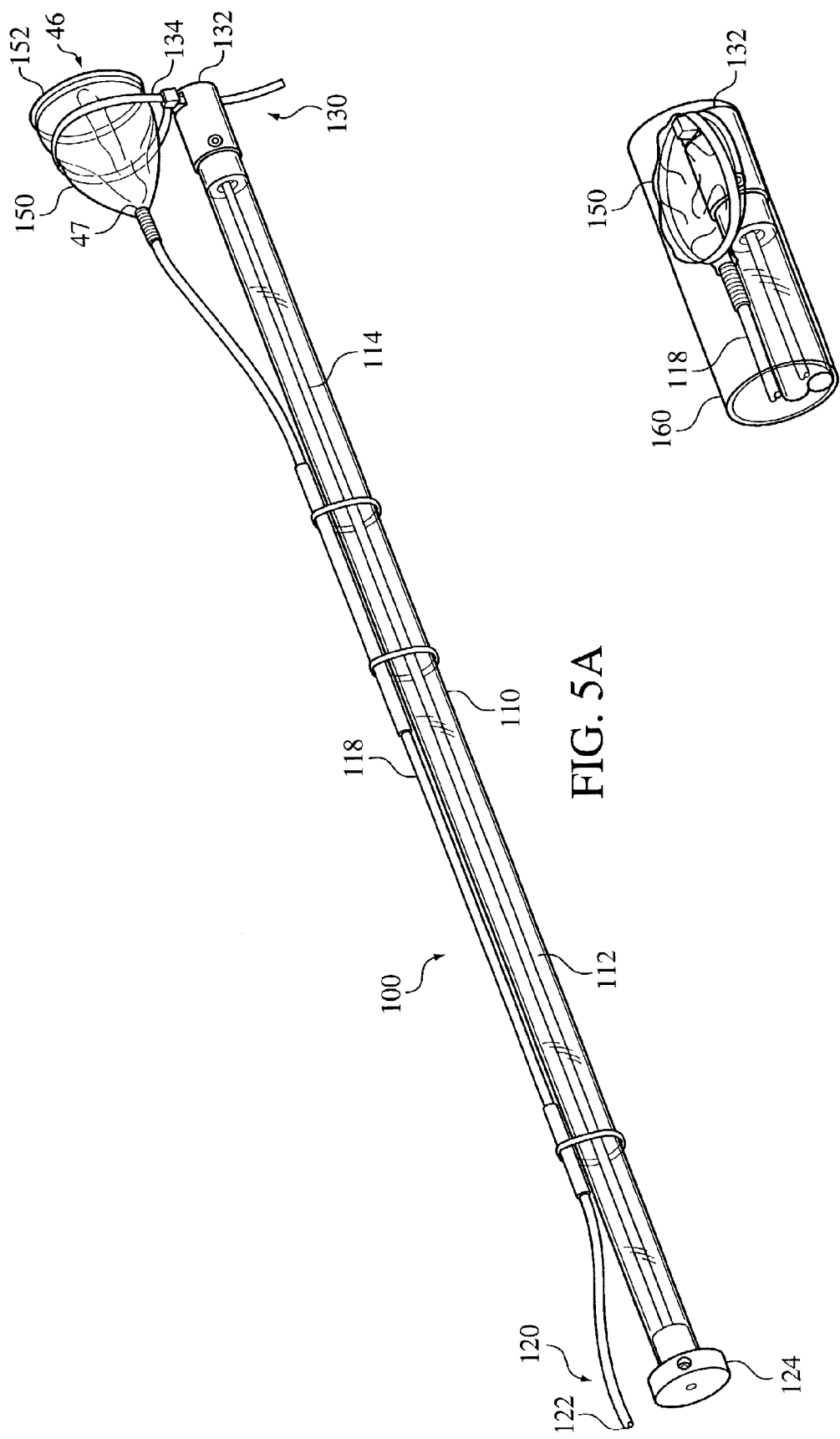

DEVICE AND METHOD OF USE FOR FUNCTIONAL ISOLATION OF ANIMAL OR HUMAN TISSUES

This application claims the benefit under 35 U.S.C. 119(e) of U.S. Provisional Application No. 60/380,630 filed May 14, 2002.

BACKGROUND

Field of the Invention

Embolic stroke is the nation's third leading killer for adults and a major cause of disability among older Americans. There are over 80,000 strokes per year in the United States alone. A common cause of embolic stroke is thrombus formation in the heart resulting from stagnant blood flow that occurs as a result of atrial fibrillation. Atrial fibrillation ("AF") is an extremely deleterious condition resulting in chaotic cardiac rhythms that typically precipitate lower cardiac output and irregular blood flow in various regions of the heart. There are over five million people worldwide with AF and about four hundred thousand new cases reported each year. Patients with AF are at approximately a 500 percent greater risk of embolic stroke due to the condition. Though pharmacologic treatments of AF are common, they are palliative rather than curative. Furthermore, a patient with AF commonly experiences a significantly decreased quality of life due, in large part, to the fear of a stroke and lifestyle restrictions associated with the attendant pharmaceutical regimen.

Patients with AF often develop thrombus in the left atrial appendage (LAA) of the heart. The LAA is a protrusion which looks like a small finger or windsock extending from the lateral wall of the left atrium between the mitral valve and root of the left pulmonary vein. The interior of the LAA is open to the left atrium allowing blood to flow from the left atrium into the appendage. The physiological function of the LAA is not fully understood. However it is known to be highly innervated indicating that it may have some neurological role. The LAA is also known to secrete substances leading to various theories of its endocrine and/or paracrine nature. Further, the LAA may function as a physical compliance chamber for the left atrium.

The LAA normally contracts with the rest of the left atrium when a heart is in a normal cardiac cycle thus keeping blood from becoming stagnant therein. But, in patients with AF, the LAA often fails to contract with any vigor or synchronicity as the result of chaotic electrical signals resulting from the pathology associated with AF. As a result, thrombus formation is predisposed to form in the stagnant blood within the LAA. Should any thromboembolic particles of this "clot" dislodge and travel to the brain, stroke occurs. Furthermore, the LAA has been demonstrated as a focal region for generation of the abnormal cardiac electrical signals causing AF. Thus, functional or electrical isolation, or both, is necessary to prevent the deleterious consequences associated with LAA pathologies secondary to AF.

Blackshear and Odell have reported that of the 1288 patients with non-rheumatic atrial fibrillation involved in their study, 221 (17%) had thrombus detected in the left atrium of the heart. Blackshear J L, Odell J A. *Appendage obliteration to reduce stroke in cardiac surgical patients with atrial fibrillation*. Ann Thorac. Surg., 1996.61(2):755-9. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke in those patients.

Pharmacological therapies for stroke prevention, such as oral or systemic administration of Warfarin or the like, are complicated by serious side effects of the medications, and patient pharmacologic noncompliance. While the most effective current palliative pharmacologic therapy for AF is Warfarin, this therapy is contraindicated in many patients, particularly the elderly in whom the risk of stroke is the highest. These issues suggest that a proactive curative local approach may be better suited to treat AF-related stroke, in contrast to a reactive palliative systemic approach.

Direct surgical and thoracoscopic techniques have been used to obliterate the LAA. Nonetheless, many patients are unsuitable candidates for such surgical procedures due to a compromised condition (e.g. mitral valve disease) or those having previously undergone cardiac surgery. Furthermore, the perceived risks of even thoracoscopic surgical procedures often outweigh the potential benefits of this treatment modality. See Blackshear and Odell above. See also Lindsay B D. *Obliteration of the left atrial appendage: A concept worth testing*. Ann Thorac. Surg., 1996.61(2):515.

Minimally invasive endovascular procedures and devices have been proposed in response to the perceived risks associated with traditional surgical procedures to address isolation or obliteration of the LAA. See, for example, U.S. Pat. No. 6,231,561 by Frazier et al. entitled "Method and Apparatus for Closing a Body Lumen" (the '561 patent). There are several problems with approaching the left atrial appendage with an endovascular catheter as shown in the '561 patent. For example, access to the left atrium is complicated and requires transeptal puncture between the right atrium and left atrium to access the LAA. This approach risks blood shunting and dislodgment of existing thrombus. Further, the endoscopic devices of the '561 patent require tissue anchors be placed into tissue being closed. The invasion of the endocardium in this manner when closing the LAA, for example, is traumatic to the tissue. Further, there are attendant inherent risks with any procedure that requires endovascular entry into the circulatory system with a medical device, such as systemic infection.

What has been needed is a less invasive atraumatic method and device for isolating, excluding, closing or occluding a target tissue, body lumen or appendage. Specifically, it would be desirable to provide an epicardial device and method for containment or elimination of thrombus formation in the LAA of patients with atrial fibrillation. The present invention satisfies these and other needs.

SUMMARY OF THE INVENTION

Accordingly, the present invention is directed to devices and methods to capture and isolate tissue. More particularly, this invention relates to devices and methods for selectively capturing, manipulating and isolating, excluding, occluding or ablating a target tissue, lumen or appendage using mechanical, electrical, radiative, chemical, or thermal energies. Preferably, the isolation, exclusion, occlusion or ablation results from a minimally invasive, external action upon the target tissue. For example, if the left atrial appendage were the target, isolation would be accomplished, in accordance with the present invention, by means of pericardial approach, gentle, non-invasive capture of the epicardial surface of the appendage (i.e. the epicardial surface is not penetrated), followed by subsequent isolation. Similarly, if the target tissue is the colonic appendage, the appendage would be accessed, in accordance with the present invention, via peritoneal approach, non-penetrating capture of the serosal surface and subsequent isolation, for example, by any of the various means discussed further below.

A further aspect of the present invention is directed to devices and methods for functional isolation of tissue, by mechanical and/or electrical, radiative, chemical, or thermal means. Particularly, isolation of the left atrial appendage (LAA), preferably by external/epicardial capture, manipulation, stabilization, and attachment of a closure device to the base of the LAA. One purpose of mechanically occluding the orifice between the LAA and the left atrium is to prevent formation within, or passage of embolic material from, the LAA into the left atrium and hence, into the bloodstream of a patient. Entry of these emboli into the patient's blood stream can have deleterious consequences including cerebral stroke.

There is provided in accordance with one aspect of the invention, an apparatus having a capture chamber that substantially encompasses the target tissue, lumen, or appendage. The capture chamber can take a variety of forms depending on the type of medical procedure and surgical approach undertaken. For example, in a conventional open chest procedure to isolate the LAA, the capture chamber may be of fixed construction (e.g., non-collapsible or rigid) and may be connected directly to a source of negative pressure. Alternately, if a minimally invasive, (i.e. closed-chest) procedure is undertaken to isolate the LAA, the capture chamber may be provided in a collapsed state for subsequent deployment when it is adjacent to the LAA. In the collapsed embodiment, it is preferable for the chamber to be connected to the distal end of an extension to facilitate placement, and to a source of negative pressure for fixation of the device to the epicardial tissue.

Apart from the structural characteristics of the capture chamber (e.g. collapsible or non-collapsible), the chamber will preferably contain an intake port and an aspiration port. The intake port will preferably contain a flexible cup-like structure disposed around the interior perimeter of the rim of the opening. The cup-like structure is preferable oriented in a convex manner relative to the interior of the capture chamber. The inner rim of the intake port is preferably comprised of a spring-reinforced soft polymeric material that allows gentle passage of the target tissue or appendage into the chamber and facilitates a seal between the port and the surface of the target tissue. Alternately, the intake port of the capture chamber may itself be a flexible cup-like structure.

In a procedure to isolate the LAA, the intake port preferably has a transverse dimension and shape sufficient to accommodate the patient's LAA. The volume of the lumen of the LAA, along with the orifice between the LAA and the left atrium, can vary remarkably. It has been reported that dimensions of the human LAA range in volume from 0.7 ml to 19.2 ml, and that the orifice's minimum opening ranged from 5 to 27 mm and a maximum diameter from 10 to 40 mm. Furthermore, the length of the LAA was reported as ranging from 17 mm to 51 mm. Therefore, a capture chamber having an intake port constructed in accordance with this invention will range in size, shape, volume and dimension to accommodate each of the above ranges, as well as other size/capacity restrictions known to one skilled in the art.

The intake port is preferably configured to sealingly engage the epicardial surface of a patient's heart. Upon the application of a negative pressure (i.e., a vacuum) to the chamber, (e.g. via an aspiration port) the structure around the intake port suctionally engages the epicardial surface of the heart and preferably proceeds to achieve a seal around the base of the appendage, thus stabilizing the structure for further manipulation. The aspiration port is preferably connected via a connecting tube to a source of adjustable negative pressure that is under the control of the physician to further facilitate capture, manipulation and release of the target tissue.

In all of the capture devices and methods of the present invention, it is preferable to accomplish the capturing step without adversely impacting the patient. For example, when using the capture chamber (described above) or the texture pins (described below) to capture the LAA, it is preferable to achieve capture and stabilization of the appendage without expelling any embolic material contained within its lumen.

The capture chambers of the present invention may further include an integral clamping device or clamping means that can be deployed around the base of the LAA while the appendage is within the capture chamber. The clamping device or means may include metallic, polymeric, or biodegradable jaws, of various surface textures and geometries, to engage the outer periphery of the appendage being isolated or occluded. The clamping device (or means) serves to atraumatically or traumatically secure or restrict the outer periphery of the surface of the base of the left atrial appendage so as to prevent the passage of embolic material or other materials through an inner passageway. The clamping means will typically be a structure comprised of a material with appropriate biocompatibility, mechanical, electrical, thermal or radiative characteristics, depending upon the application. Typical examples of suitable materials for the clamping device (or means) include titanium, medical-grade stainless steel, or various known polymeric compounds, for example, high-density polypropylene, or poly-1-lactic acid (PLLA)-, polyglycolic acid-, polycaprolactone-, polyorthoesther-based compounds.

In an alternate embodiment, a device having features of the invention will include a pair of moveable textured pins for capturing, manipulating and mechanically and/or electrically occluding the LAA. The pins are preferably configured to atraumatically engage, position and stabilize the epicardial surface of the LAA. For example, the pins may start in close parallel relation to one another and be capable of lateral planar separation. In this way, the pins can be separated to create a gap or opening of an appropriate size to receive or capture the LAA. Each of these pins are preferably capable of independent axial rotation.

It is most preferable if the pins are capable of a wide-range of spatial orientation and movement to facilitate capture of the LAA. Once separated by the appropriate distance, the textured pins preferably rotate to "draw-in" the appendage. For example, one pin may rotate in a clockwise direction and the other may rotate in a counter-clockwise direction. Alternately, the pins may move independently—such that one pin remains fixed while the other rotates. Additionally, it is preferable if the pin-holder device is itself axially rotatable to allow one pin to sweep an arc relative to the other pin. In all spatial orientations, it is preferable if the pins remain in parallel relation relative to one another.

Once the pins are positioned at the base of the LAA, they may be moved together in a lateral planar direction to decrease the distance between the pins and thereby secure and maintain the position of the LAA. These pins may then be irremovably engaged to one another to form a clamping device which will be disengaged from the apparatus and remain securely in place at the base of the LAA. Alternatively, a separate clamp would be positioned and secured at the base of the LAA. This clamp would thereby occlude the passage of embolic material from the lumen of the LAA to the chamber of the left atrium.

In an alternate absorbable embodiment, the clamp may be used to initiate an inflammation response via the imposition of mechanical or other stress upon the tissue. Healing that occurs as a result of this imposed wound will mechanically occlude the orifice of the LAA to prevent passage of blood and/or emboli between the appendage and the heart chamber. This absorbable clamp would preferably remain securely in place during the temporal period of healing and then subsequently dissolve.

Another aspect of the present invention includes the electrical isolation of the LAA to prevent conduction of the chaotic electrical signals that originate in the LAA to other areas of the heart. Devices constructed in accordance with the invention are usable in either traditional or minimally invasive surgical approaches. An endoscopic-based epicardial approach to LAA isolation provides several advantages over both transluminal vascular catheterization and traditional surgical techniques such as thoracotomy or median sternotomy.

Because of the role the LAA plays in hormone production, a method of isolating the lumen to prevent emboli from forming or exiting the LAA, while maintaining vascularization of the appendage myocardium, is also provided.

In addition to physical isolation via mechanical means, it is also desirable to achieve electrical isolation because of the role that the LAA may play in the pathogenesis of AF. For example, since the LAA is a focus of disruptive electrical activity that may contribute to the pathogenesis AF, it would be desirable to isolate this activity. One means of achieving electrical isolation is to create a lesion using a combination of mechanical, electrical or thermal energy, to prevent the disruptive electrical signals from propagating to other areas of the heart.

Bipolar electrodes have achieved wide acceptance by surgeons for a variety of electrosurgical procedures. Electrosurgical techniques are generally divided into two classes, namely monopolar techniques and bipolar techniques. In monopolar procedures, the electric current flux of the active electrode passes through the patient's body to the return electrode. In bipolar procedures, the electromagnetic wave flows from an active electrode to another active electrode through a limited amount of tissue between the two electrodes.

Modern electrosurgical equipment produces an electromagnetic wave of a very high frequency that reaches between 350,000 cps (cycles/second or 350 kilohertz) and 4,000,000 cps (4 MHz—megahertz). The wave used in electrosurgeries is in the mean of the frequency used in the FM radio, and thus, electrosurgical waves are frequently called radiofrequency (RF) waves. Because bipolar electrodes provide for the passage of electromagnetic energy between two (2) active electrodes in a directionally controllable manner, it is possible to use higher frequency energy because it can be directed. Consequently, the loss of energy that radiates to un-targeted areas (such as tissue surrounding the target site) is minimized through the use of bipolar electrodes.

The three main effects caused by radio frequency waves passing through biologic tissues are the Faradic effect, the electrolytic effect and the thermal effect. The Faradic effect is not usually observed with modern electrosurgical equipment that can achieve frequencies above 300 kHz. The electrolytic effect is caused by the polarization of ions in a tissue. When an alternating current is applied to a tissue composed mainly of water and electrolytes, the ionized particles in the tissue will vibrate, thereby increasing kinetic energy. Due to the high frequency applied through the alternating current, the ionized particles will move only slightly, but the kinetic energy will ultimately lead to a temperature increase in the tissue.

There are several factors that influence the mode of conduction of heat through a tissue (i.e. the thermal effect). Water is an excellent medium to maintain thermal balance in a tissue because of its constant vaporization temperature. Another important factor is the vasculature of the tissue, since circulation helps dissipation of heat. Thus the effects caused by a temperature rise in biologic tissue will depend both on the final temperature that is reached and the total duration an elevated temperature is maintained. When the temperature rises slowly, the tissue will dry out and there will be coagulation of constitutive proteins. In contrast, when the tissue is quickly heated to high temperatures neither vaporization or thermal transference will effectively dissipate heat, and therefore, tissue temperatures will rise above 100° C. Intracellular water vaporization will produce a volume increase and subsequent cell membrane rupture due to excessive internal pressure. Several factors, including water content, will influence the electrical resistance of tissues. The electrical resistance of dry tissue is much higher than that of well hydrated tissue. It may be preferable to employ a conductive fluid, such as saline, during application of the RF energy.

The bipolar electrodes of the present invention are preferably incorporated into the rotatable pins of the device. This allows the LAA to be captured, positioned, and electrically isolated using a single device and in a single operational step. Control of a device having biopolar electrodes may be accomplished, for example, by the circuitry and teaching found in U.S. Pat. No. 6,203,541 to Keppel ("the '541 patent"), which is incorporated herein by reference for these teachings. Further, the electrodes are preferably connected through the central circuitry to an external radio frequency power supply.

In addition to the various closure means presented herein, an embodiment of a closure device having a pharmacological agent associated with the surface thereof is also contemplated. For example, U.S. Pat. No. 5,282,844 discloses steroid eluting electrodes, and is incorporated herein by reference for this teaching.

An additional embodiment includes the use of an integrated system to effectively visualize the LAA or other tissues to be closed. Endoscopes have been used for many years in the medical field for viewing within a desired region of the patient's body through the patient's airway, other natural orifices, or a surgical incision. An endoscope typically has an elongated flexible probe fixed to a housing at its proximal end. Additionally, an endoscope may have a medical device or assembly attached to its distal end for carrying out a specific procedure or function. Optical fibers typically extend the length of the endoscopic probe and carry an image from the distal end of the probe to the housing, where it can be viewed through an eye piece by the physician. The housing generally includes one or more controls allowing the physician to direct the distal tip of the probe in a desired direction. The probe can also be equipped with one or more instrument channels for surgical implements. Additionally, a suction channel normally extends the length of the endoscopic probe to facilitate removal of mucus, blood, or secretions that can obstruct the physician's view or interfere with endoscopic surgery.

There is provided in accordance with one aspect of the present invention, an endoscopic device for functionally isolating the left atrial appendage from fluid and electrical communication with the left atrium of a patient while maintaining the capillary blood flow carrying hormone produced in the LAA tissue. It is contemplated that by using the devices and methods in accordance with the present invention, following the occlusion of the orifice of the LAA, the appendage can optionally remain viable. Viability is defined as capillary blood flow to the myocardium and hormonal exchange between the appendage and surrounding tissue. It is most preferable if the lumen of the LAA can be isolated with the endoscopic devices of the present invention without destroying the vascularization of the tissue of the appendage.

Generally, an endoscopic device in accordance with the present invention will include an elongated extension having a proximal and distal end. The proximal end of the extension preferably contains a controller unit that can manipulate and implement an assembly located at the distal end of the extension. Preferably, the extension will include optical fibers extending its length to carry a visual image from the distal end of the extension for viewing and to assist the physician in manipulating the assembly at the distal end. Preferably, the assembly can capture, stabilize, and (mechanically and/or electrically) isolate the LAA. This isolation process may be accomplished, for example, by way of a capture chamber or via a textured pin-based clamping device as described previously herein. The endoscopic device integrated with the capture devices of the present invention and the methods of the present invention, are applicable to a variety of surgical procedures and approaches for isolation of animal and human tissues, lumens, or appendages.

In accordance with a further aspect of the present invention, there is provided an endoscopic device for occluding the left atrial appendage (LAA) of a patient. The device is comprised of a probe-extension with a controller at its proximal end to allow spatial manipulation of a distal assembly. The controller is preferably operable wherein initiation of an action upon a trigger or switch of the controller will cause a corresponding reaction to an assembly or component attached to the distal end of the probe/extension. For example, operation of a trigger at the proximal end of the probe may facilitate placement or deployment of a collapsible capture chamber, or alternatively, separate a pair of rotatable pins in a lateral coplanar direction. Additional switches/triggers may generate suction controls, rotation controls and/or light sources, as well as deploy clamping devices or disengage the removable pin-clamp assembly.

In accordance with a further aspect of the present invention, there is provided a method of mechanically isolating the orifice of the left atrial appendage. The method comprises the steps of accessing the LAA, capturing the LAA and attaching a closure device to the base of the LAA. Access to the LAA is preferably epicardial access, either through open-chest or minimally invasive approaches.

A method is provided of electrically isolating the tissue of the left atrial appendage in accordance with a further aspect of the present invention. The method comprises the steps of accessing the LAA, capturing the LAA, and transmitting an electrical, thermal, or mechanical energy of sufficient amplitude and duration to create a transmural lesion to isolate the LAA tissue. Access to the LAA is preferably epicardial access, either through open-chest or minimally invasive approaches.

The step of electrically isolating a body appendage, for example the colonic appendage, may comprise peritoneal introduction of a device into the abdomen, positioning the capture assembly adjacent the appendage; capturing the appendage; positioning the bipolar electrodes adjacent the target; and applying sufficient RF energy to the bipolar electrodes to isolate, exclude, occlude or ablate the appendage.

Preferably, the capturing step comprises non-invasively securing the appendage within a capture chamber through the use of suction. In an alternate embodiment, the appendage may be gently captured with rotating textured pins that are separable and act to draw in the appendage by rotation of these textured pins.

The closure devices to be used in accordance with the methods of the present invention may include sutureless clamps that provide closure via bilateral or circumferential pressure. For example, a bilateral clamp constructed of appropriate biomaterial may be applied at the base of the LAA to "squeeze" the opening closed simultaneously imposing a mechanical stress to initiate a healing response. After the orifice of the LAA has healed shut the biomaterial-based clamp harmlessly dissolves. Alternately, a substantially circular clamping device may be employed to ensnare the appendage and close the opening by compressing the periphery of the base of the appendage while still permitting capillary blood flow to the LAA for hormone exchange.

The step of deploying the clamping device is preferably accomplished after capturing and stabilizing the base of the LAA using a separate or integral extension device. For example, the device and methods of U.S. Pat. No. 5,984,917 to Fleischman et. al., would be readily adaptable to the present invention. In practicing the methods of this invention, the clamp is preferably positioned at the base of the LAA and engaged to compress the base of the LAA in a secure and permanent manner. Additionally, a feedback mechanism and/or sensor associated with the clamp may preferably provide the surgeon with an indication of the amount of mechanical force applied by the clamp to allow tailoring to a particular degree of functional isolation. For example, piezoelectric crystals or another strain gauge device could be embedded into the rotatable pins such that material stress as a result of applied force causes a voltage potential. This voltage potential would be proportional to the amount of applied force and could be transduced from the apparatus for display to the physician using vibration, sound, or visual methodologies. After proper deployment, the clamp may preferably be detached from the extension device and remain securely in place.

BRIEF DESCRIPTION OF THE DRAWINGS

For the present invention to be clearly understood and readily practiced, it will be further described in conjunction with the following figures, wherein like reference characters designate the same or similar elements, and which figures are incorporated into and constitute a part of the specification, wherein:

FIG. 5A is a perspective view of a medical device having a collapsible capture chamber in accordance with one embodiment of the invention.

FIG. 5B is a perspective view of a stowed collapsible capture chamber prior to deployment.

DETAILED DESCRIPTION OF THE INVENTION

It is to be understood that the figures and descriptions of the present invention have been simplified to illustrate elements that are relevant for a clear understanding of the invention, while eliminating, for purposes of clarity, other elements that may be well known. Those of ordinary skill in the art will recognize that other elements are desirable and/or required in order to implement the present invention. However, because such elements are either well known or well within the skill of the art, and because they do not facilitate a better understanding of the present invention, a discussion of such elements is not provided herein. The detailed description will be provided hereinbelow with reference to the attached drawings.

Figure 1:
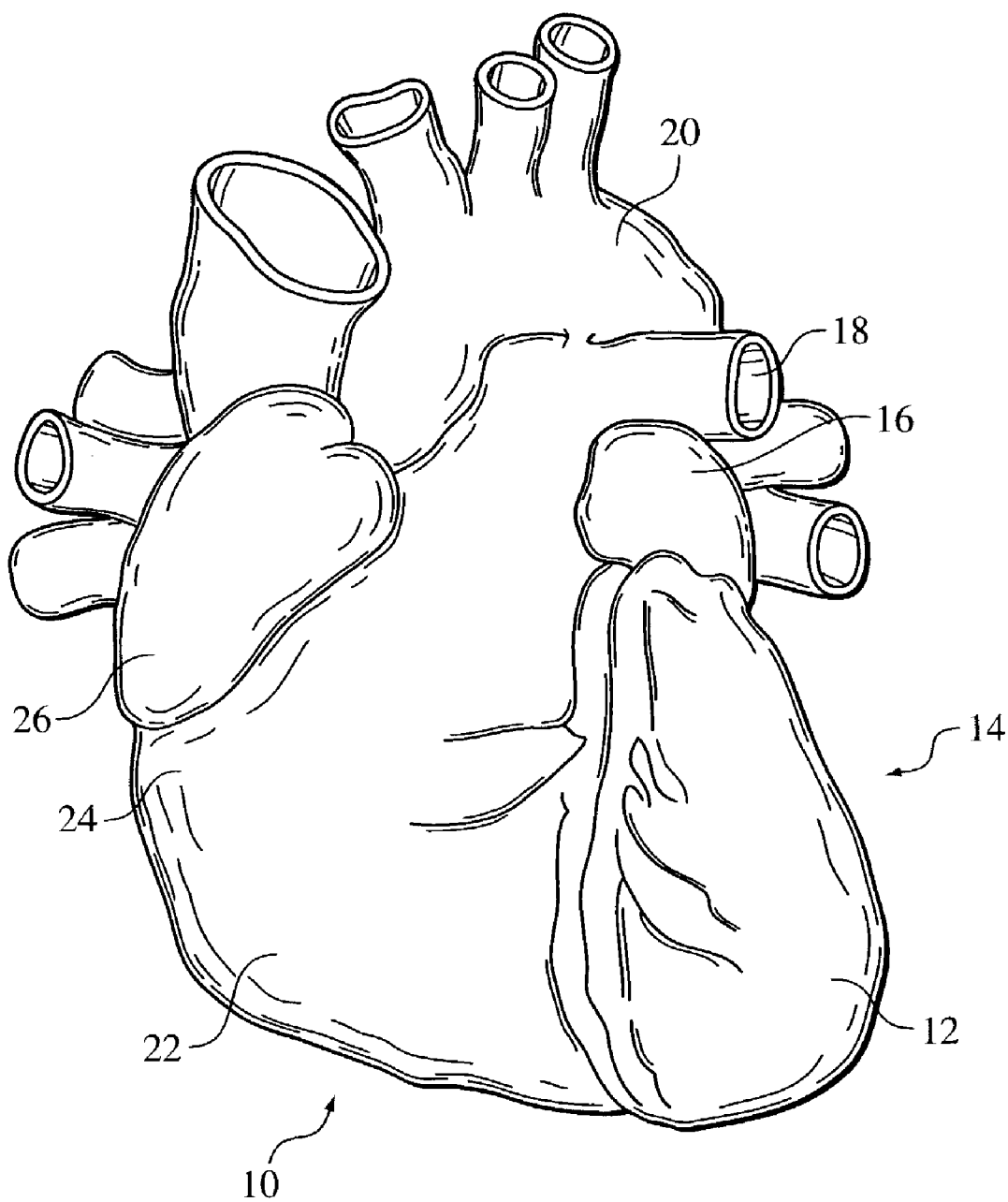
FIG. 1 is an anterior illustration of a heart with the proximal parts of the great vessels.

Referring to FIG. 1, a heart 10 is illustrated to show certain portions including the left ventricle 12, the left atrium 14, the left atrial appendage (LAA) 16, the pulmonary artery 18, the aorta 20, the right ventricle 22, the right atrium 24, and the right atrial appendage 26. As is understood in the art, the left atrium 14 is located above the left ventricle 12 and the two are separated by the mitral valve (not illustrated). The LAA 16 is normally in fluid and electrical communication with the left atrium 14 such that blood flows in and out of the LAA, and electrical impulses conduct to and from the LAA 16 as the heart 10 beats.

Figure 2:
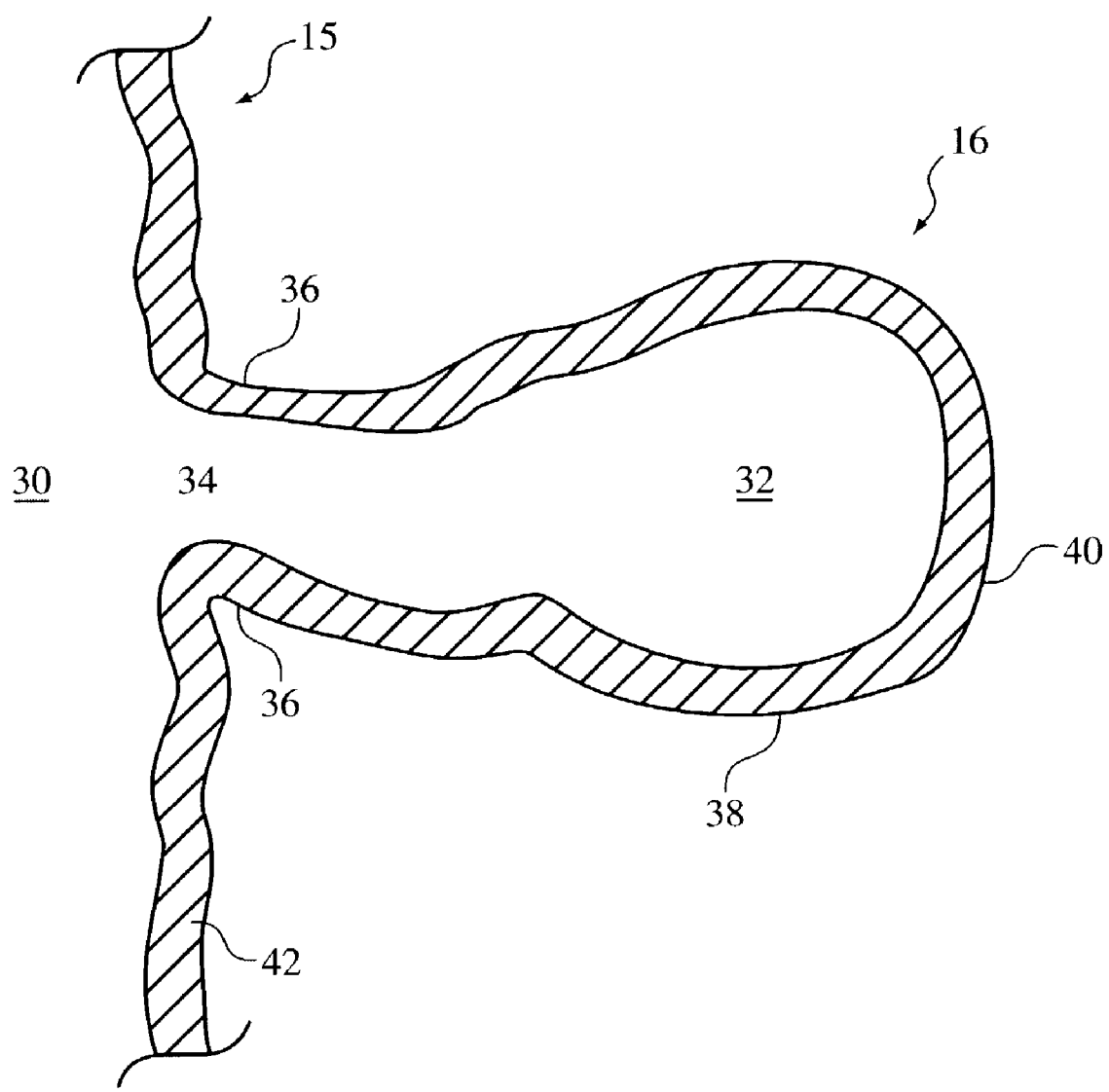
FIG. 2 is a schematic cross-sectional view of the left atrial appendage (LAA).

FIG. 2 is a schematic cross section of the LAA 16. The chamber of the left atrium 30 and the lumen 32 of the LAA 16 are shown in communication via orifice 34. The LAA is further defined as having a base portion 36 proximal to its attachment with the epicardial surface of the left atrium 30, and a body portion 38 distal to the point of attachment of the appendage 16 with the left atrium. The walls 40 of the LAA 16 are vascularized heart tissue substantially similar to the walls 42 of the left atrium.

Figure 3:
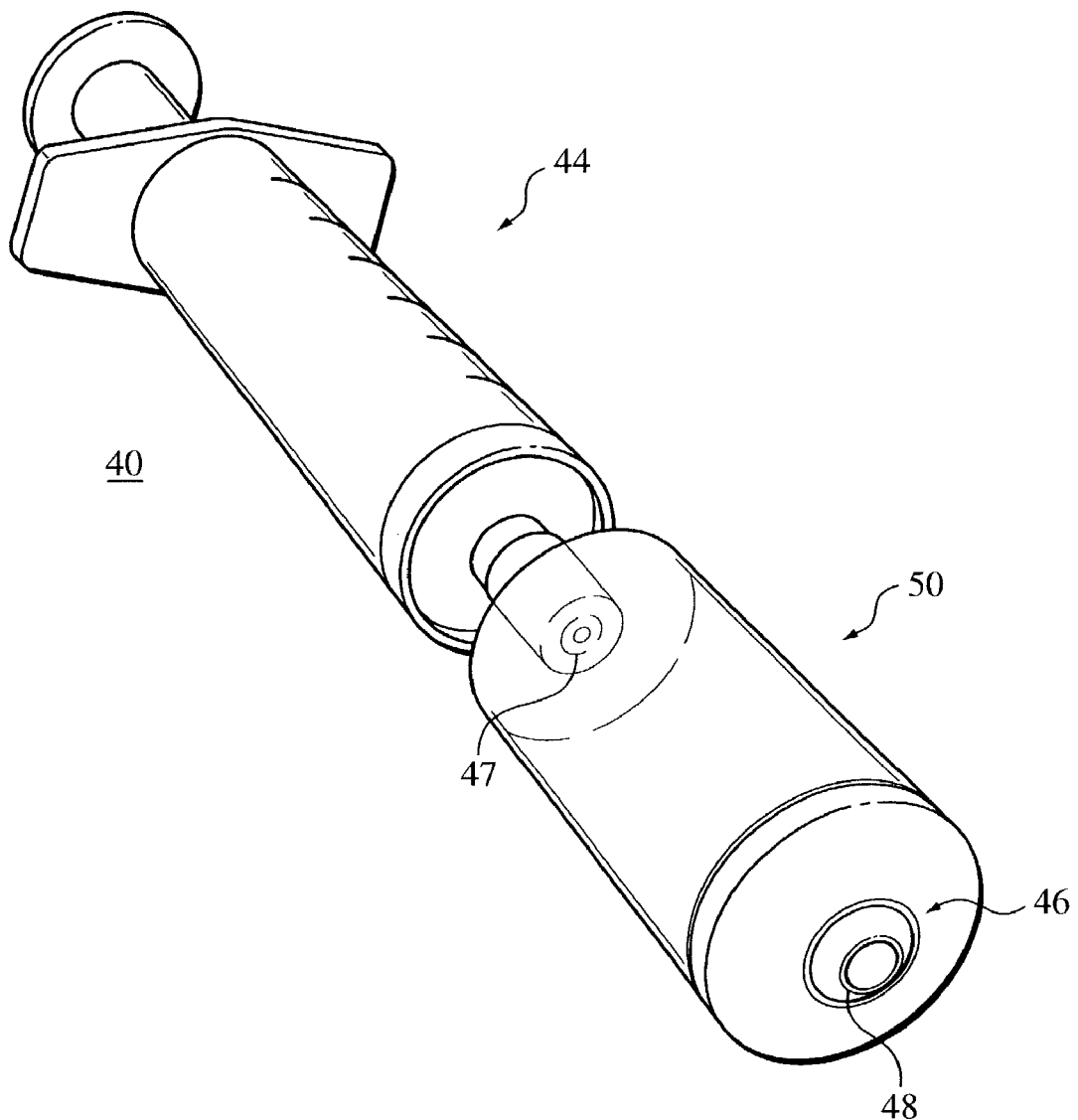
FIG. 3 is a perspective view of a device having a non-collapsible capture chamber in accordance with one embodiment of the invention.

FIG. 3 is a perspective view of one type of capture chamber device 40 contemplated by the present invention. The device is generally comprised of a vacuum source 44 attached to a capture chamber 50. In the embodiment shown in FIG. 3, the capture chamber 50 is rigid (i.e. non-collapsible) in construction, but collapsible and/or deployable chambers are also contemplated, as more fully described below.

The capture chamber 50 is shown with an intake port 46 having a flexible cup-like structure 48 disposed around the periphery of the port 46 opening. The chamber 50 is also equipped with an aspiration port 47 that connects to the vacuum source 44. Preferably, the aspiration port 47 is located on an opposite axis relative to the intake port 46.

Generally, the device 40 is used such that upon positioning the intake port 46 of the capture chamber 50 adjacent the LAA of a patient, a vacuum is applied to the aspiration port 47 causing the LAA to enter the chamber 50 via the intake port 46, as shown and discussed further below with reference to FIG. 4.

Figure 4:
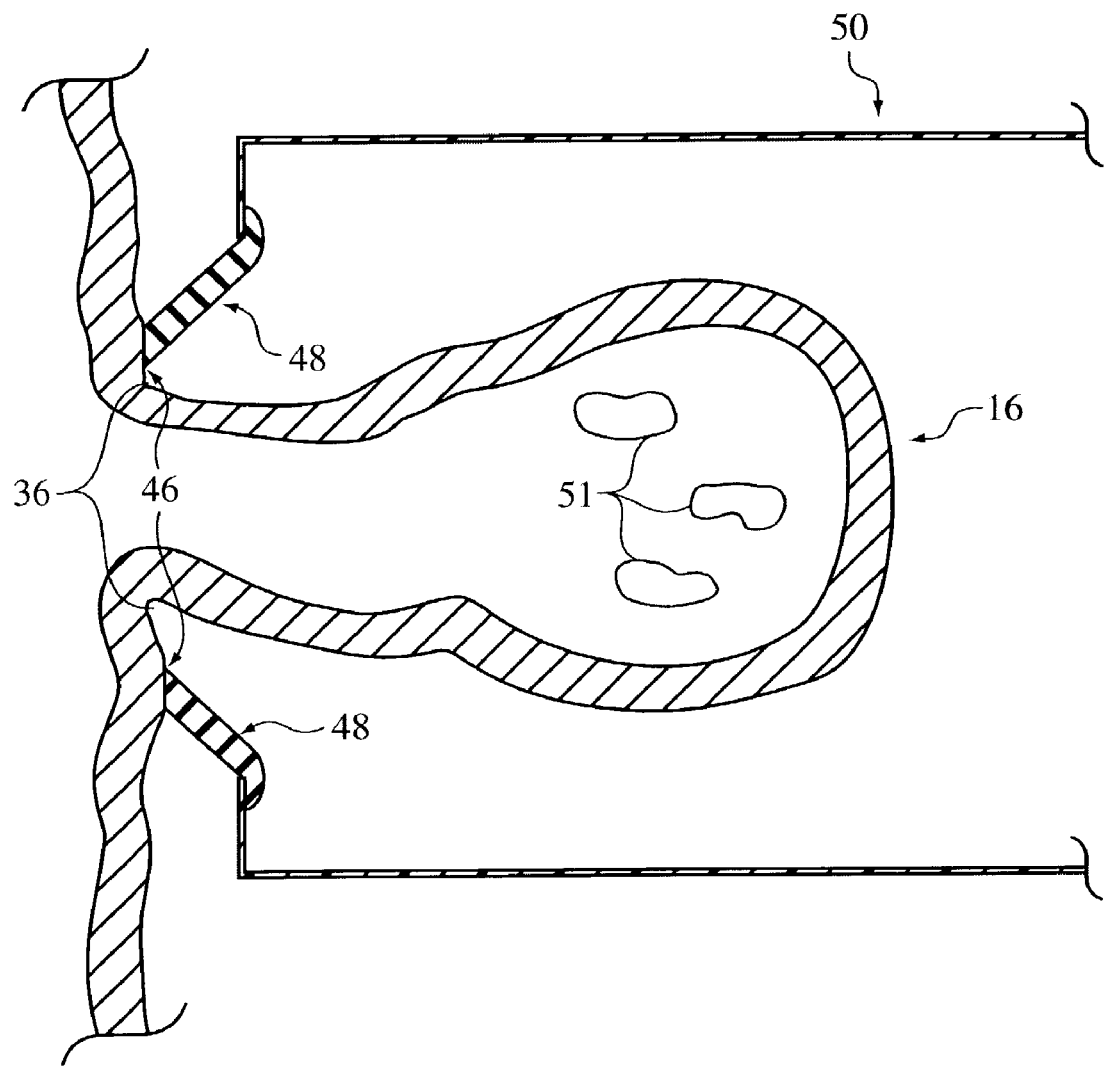
FIG. 4 is a schematic cross-sectional view of the left atrial appendage captured within a non-collapsible capture chamber of a device in accordance with one embodiment of the invention.

FIG. 4 illustrates a schematic cross section of one embodiment of the invention. The device shown is for attachment to the distal end of a medical device and includes a capture chamber 50 for capturing and stabilizing and/or immobilizing a target tissue, which in this example is the LAA 16. In the embodiment shown, the LAA 16 enters the chamber 50 via an intake port 46, for example, by being drawn into the chamber 50, when a vacuum is applied to the aspiration port (not shown) of the chamber 50. The intake port 46 is preferably comprised of a flexible structure 48 which acts to secure the base 36 of the LAA 16 without penetrating the epicardial surface of the LAA 16 and without causing emboli 51 to be expelled from the LAA cavity into the left atrium. This non-invasive, gentle-capture method preferably secures and stabilizes the LAA 16 for further procedures and manipulation, such as the attachment of a clamping or closure device (not shown in FIG. 4) to the base 36 of the LAA, as described further herein. Preferably, the intake port 46 is generally circular in shape and is a ring-like structure having a diameter of less than 50 mm.

FIG. 5A shows a further embodiment of a medical device 100 having a capture chamber 150 as contemplated by the present invention. The medical device 100 includes an elongated shaft 110 comprised of a hollow sheath 112 and having proximal 120 and distal 130 ends. At the proximal end 120, controllers and connections are preferably provided to allow for manipulation of the various components of the device provided at the distal end. Communication between the control mechanisms at the proximal end 120 and the components located at the distal end 130 of the device 100 may be accomplished by cables, pushrods 114, connecting tubes 118, or any other means capable of placing the distal-end component under the control of a surgeon at the proximal end. These means of communication (114, 118) between the proximal 120 and distal 130 ends of the device 100, may be located within the sheath 112 or adjacent to the sheath 112, such as is shown for connecting tube 118. A connector 122 for a vacuum source is preferably provided at the proximal end 120, such that the vacuum source is in operable connection with a collapsible capture chamber 150 at the distal end 130 of the device 100.

A complete device 100 further includes a deployable occlusion snare (i.e. closure device) 134 to encircle the base of the LAA. The occlusion snare 134 may be comprised of any suitable material, and it is preferable if, following deployment around the base of the appendage and constriction (as discussed below with reference to FIG. 6F), the snare is easily separable from the actuator 132. Prior to insertion of the medical device 100, it is preferable if the components at the distal end 130 of the device 100 can be "stowed" within cannula 160 for insertion through an endoscopic port, for example, as shown in FIG. 5B.

Preferably, methods of using the device 100 are by means of a sub-xyphoid pericardial access including procedures that are conducted under local anesthetic. Pericardial access without effusion has been achieved by various methodologies including sub-xiphoid access using the PerDUCER™ device from Comedicus Inc. (Columbia Heights, Minn.). In using the PerDUCER™ device, a stab incision is made in the sub-xyphoid area and a 17-gauge angled cannula with a preloaded guide wire is advanced into the mediastinal space. After cannula removal, a 19 Fr. is inserted over the wire and the PerDUCER™ device is positioned such that an isolated portion of pericardium is captured by suction. A sheathed needle is then advanced which punctures this isolation portion allowing pericardial access. A similar access methodology for deployment of the proposed devices of this invention are contemplated.

With further reference to FIG. 5A, the collapsible chamber 150 is preferably made out of flexible polyurethane-type material. The chamber 150 is also equipped with an aspiration port 47 that connects to the vacuum source. Preferably, the aspiration port 47 is located on an opposite axis relative to the intake port 46. When fully deployed, the intake port 46 of the collapsible chamber 150 may range between 10 and 40 mm, preferably between 12 and 30 mm, and most preferably between 16 and 22 mm. The opening may further be comprised of a rim 152 of nitinol wire, or other similar material, to maintain the position of the opening for deployment.

Figure 6A:
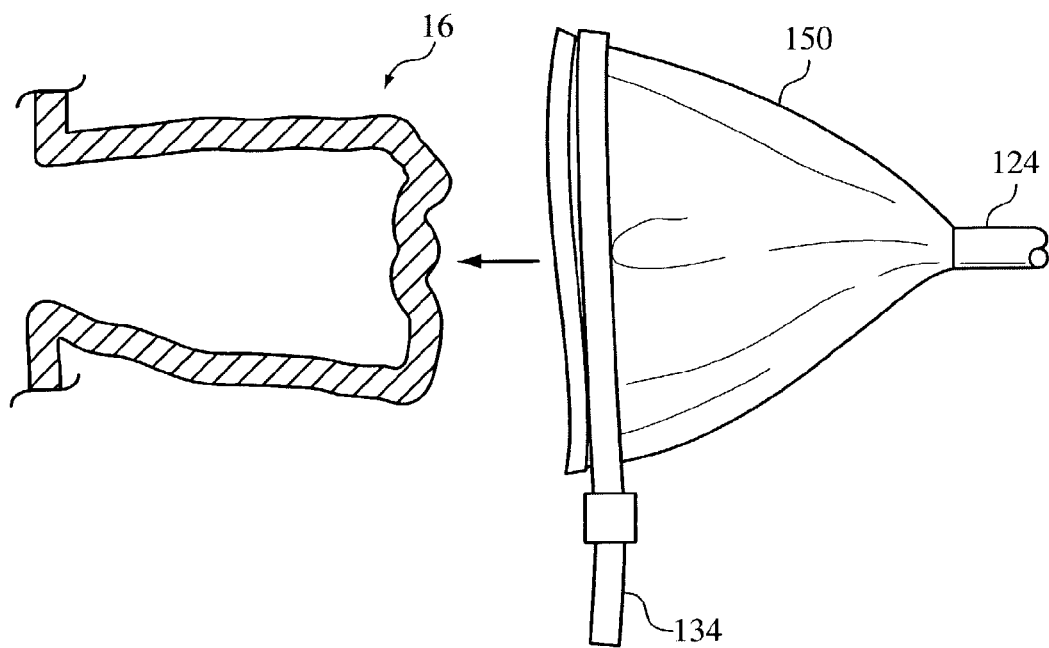
FIGS. 6A-F are a series of schematic illustrations showing one method of operation of the medical device shown in FIG. 5.
Figure 6B:
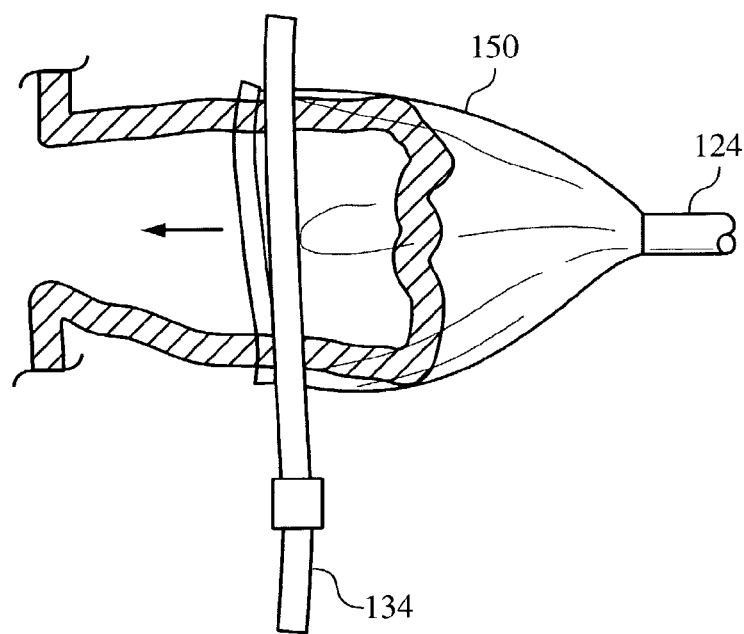
Figure 6C:
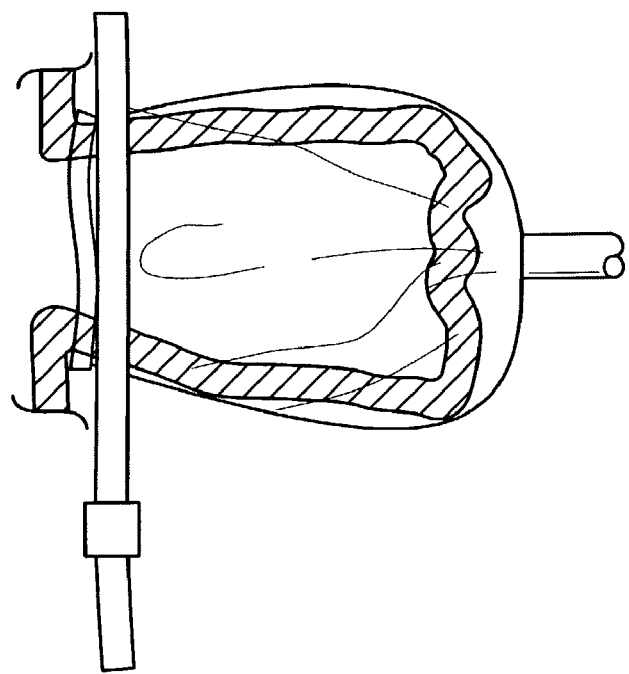
Figure 6D:
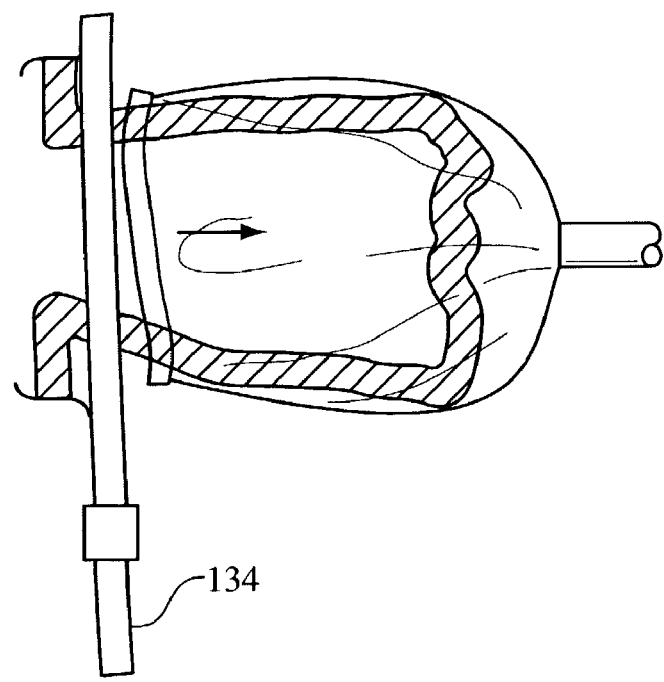
Figure 6E:
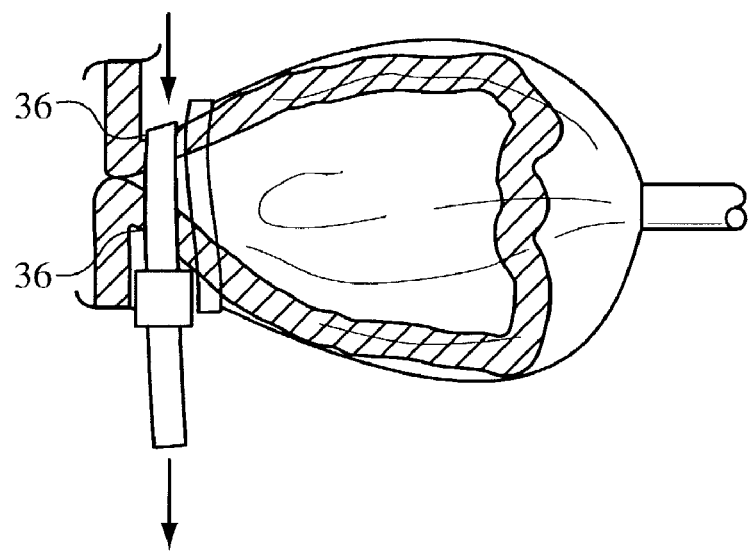

A rotatable knob 124 is also provided in operable connection with a clamp actuator 132 such that, for example, when the knob 124 is rotated in a clockwise direction, the clamp 134 at the distal end 130 of the device 100 is drawn closed, as further shown in FIG. 6E. Similarly when the knob 124 is rotated in a counter-clockwise direction, the clamp 134 is released from the actuator 132.

Figure 6F:
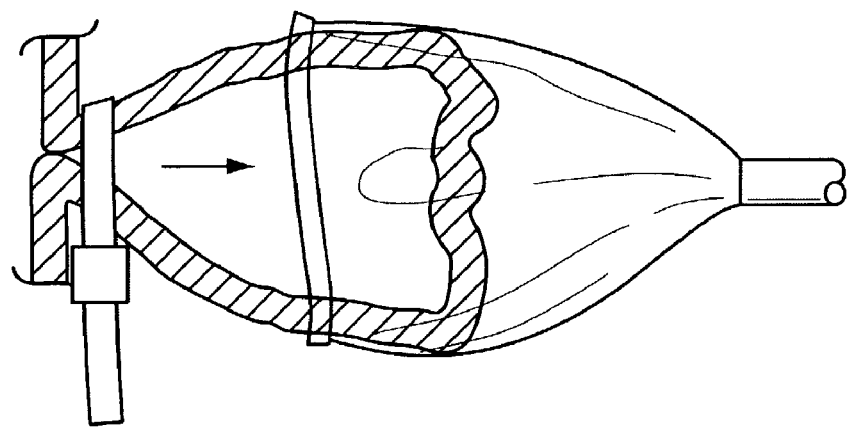

With reference to FIGS. 6A-F, the device 100 of FIG. 5 and a method of its use are further illustrated. FIG. 6A is a schematic sideview showing the collapsible capture chamber 150/closure device 134 assembly approaching the LAA 16 for initial capture of the appendage. Upon the capture chamber 150 coming into proximity with the appendage 16, a vacuum is applied to the connecting line 124 such that the collapsible chamber 150 conforms to the appendage 16 and allows the chamber 150 to be suctioned over the appendage 16 as the device proceeds to be advanced, as shown in FIGS. 6B and 6C. Once the appendage 16 has been fully captured in the collapsible chamber 150 (FIG. 6C), the appendage 16 can be further manipulated and isolated. For example, as shown in FIG. 6D, the appendage 16 can be manipulated (withdrawn) from the circumference of the closure device 134, wherein, upon this re-positioning, the closure device 134 can be drawn together around the base 36 of the appendage 16, as previously described and as shown in FIG. 6E. After clamping the base 36 of the appendage 16 to isolate its contents, the vacuum being supplied by connecting line 124 can be decreased or discontinued and the collapsible chamber 150 attached to the device (not shown) can be withdrawn, as shown in FIG. 6F.

Figure 7:
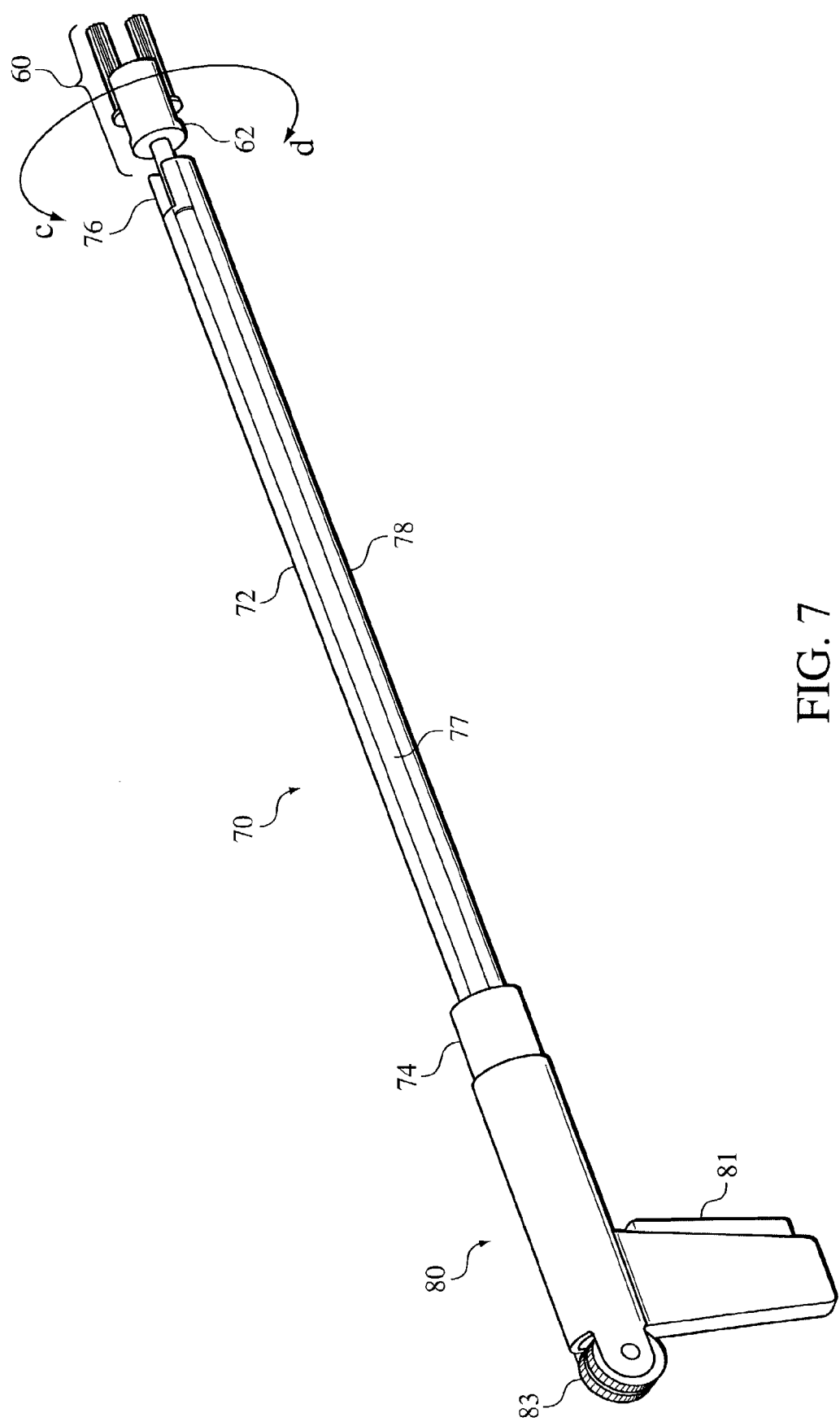
FIG. 7 is a perspective view of a medical device in accordance with one embodiment of the invention.

FIG. 7 shows a medical device in accordance with another preferred embodiment of the present invention. The device 70 is comprised of an extension 72 having a proximal end 74 and a distal end 76. The extension 72 may be a flexible wire 77 contained within a bendable sheath, for example, or a preferably stiffened hollow sheath with little or no flex. This sheath is movable once the LAA or similar tissue is captured to facilitate the distal assembly 60 to move with the tissue. The device 70 further includes a rigid clamp beam 78 that functions to stabilize the flexible extension 72 during insertion into the patient and subsequent capture and stabilization of the target tissue. Following insertion of the device 70 into the patient, the clamp beam 78 may be removed such that the flexible extension 72 and pin holder 62 can move independently to allow maximum surgical flexibility and control. The assembly 60 as shown in FIG. 8 is one embodiment that is preferably comprised of a pin holder 62, having sub-components such as a textured first pin 64 and a textured second pin 66. Alternatively, the assembly 60 may be of a type and design comprised of a capture chamber as previously shown in FIG. 3 or 5, for example.

Figure 8A:
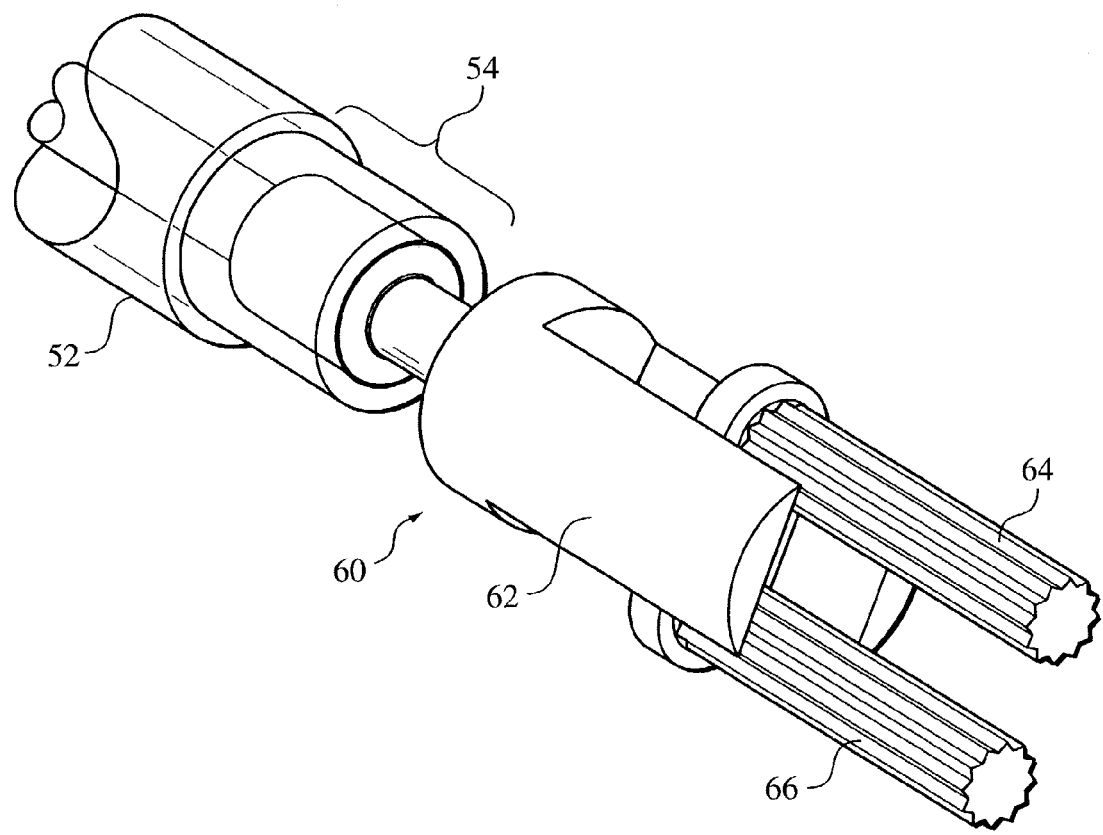
FIGS. 8A-B are perspective views and schematic illustrations of an assembly for the epicardial capture, stabilization and isolation of the LAA in accordance with one embodiment of the invention.

FIG. 8A shows another embodiment of an assembly 60 for attachment to the distal end of a surgical instrument. The assembly 60 is comprised of a pin holder 62, a first textured pin 64 and a second textured pin 66. The pin holder 62 is preferably capable of axial rotation and is moveable in a plane transverse to the longitudinal axis of the shaft 52. The pins 64, 66 are held by the pin holder 62 in a substantially parallel relationship along their longitudinal axis relative to each other. In this view, the sub-components of the pin holder 62 (e.g., the pins 64, 66) are shown in an open parallel relation to one another. Pins 64 and 66 are preferably moveable (separable) in a plane perpendicular to their longitudinal axis (i.e. lateral planar movement) such that they can be maintained in a closed parallel relation prior to deployment. The pin holder 62 is preferably attached to the distal end of the shaft 52 by a controllable universal joint 54 which provides for axial rotation as well as transverse planar movement of the pin holder 62. It is also preferable for pins 64, 66 to be capable of independent axial rotation.

Figure 8B:
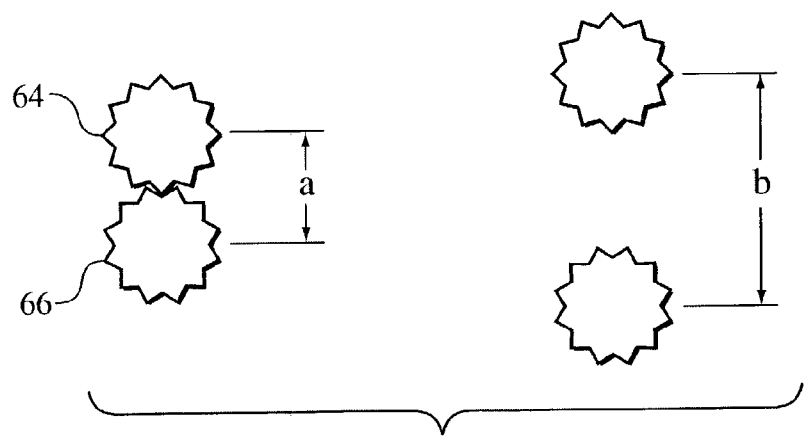

FIG. 8B shows an end view of pins 64, 66 in two positions. The textured pins 64, 66 may be inserted into a patient via a surgical port or other surgical access to the LAA, for example, in position "a" and then be subsequently deployed (separated), for example, to position "b" prior to positioning the pins 64, 66 adjacent the target tissue. Upon completion of the procedure (e.g. isolation of the target tissue) and before assembly 60 is removed from the patient, pins 64, 66 may be returned to position "a". In an alternative embodiment, the pins 64, 66 may also comprise the closure/clamp device that acts to mechanically and/or electrically functionally isolate the LAA, as discussed further herein.

Figure 9A:
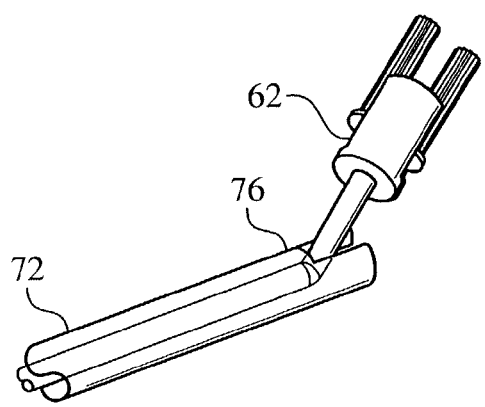
FIGS. 9A-C are a series of illustrations showing the operation and articulation of a device in accordance with one embodiment of the invention.
Figure 9B:
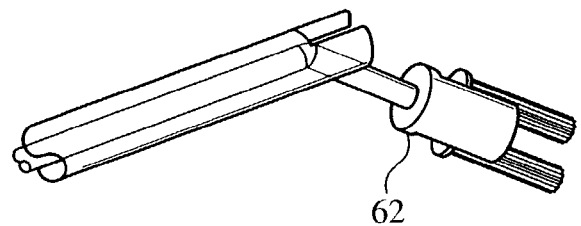
Figure 9C:
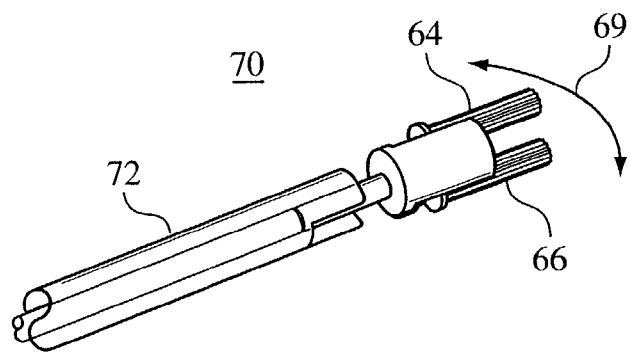

FIGS. 9A-C further illustrate an assembly for isolating a target tissue, body lumen or appendage of a patent in accordance with one aspect of the present invention. The device is comprised of a shaft 72 with a pistol-grip type of controller 80 for example, as shown in FIG. 7 attached to its proximal end 74. Any variety of controllers, now known or later developed, are contemplated in conjunction with the present invention. For example, the trigger/control mechanisms contained within the controller may be mechanical, electromechanical, servos, robotic, microprocessors or any combination thereof.

The assembly of FIG. 9A also includes a pin holder 62 attached to the distal end 76 of the shaft 72. In this embodiment illustrated in FIG. 9 and with reference to FIG. 7, the pin holder 62 is connected to and under the operable control of the controller 80 such that the pin holder 62 is moveable in a plane transverse to the longitudinal axis of the device 70. For example, by operator action upon a trigger (e.g., 81, 83) the pin holder 62 is preferably moveable between position "c" and position "d" as shown in FIG. 7. The process of moving pin holder 62 in a plane transverse to the longitudinal axis is shown further in FIGS. 9A-C. For example, by rotating the device 70 by 90°, the "up-down" transverse movement 69 shown in FIGS. 9A-B becomes the "side to side" transverse movement shown in FIG. 9C.

The sub-components 64, 66 preferably move (open and close) in a plane perpendicular to the longitudinal axis of the shaft 72. This lateral planar movement of the pins 64, 66 preferably can occur in a bilateral sense such that the pins can open or close simultaneously to alter the distance between the pins 64, 66. Alternately, the pins may operate unilaterally.

Figure 10:
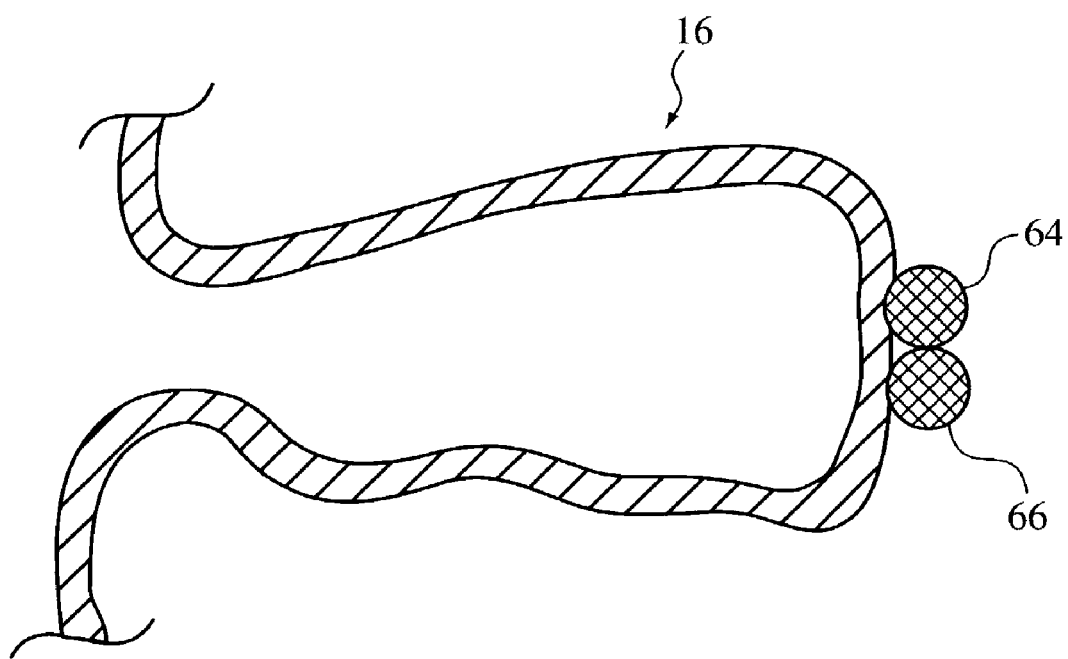
FIG. 10 is a schematic cross-sectional view of the LAA showing the textured pin placement of a capture device as shown in FIG. 7, prior to deployment of the pins and subsequent capture of the LAA.
Figure 11C:
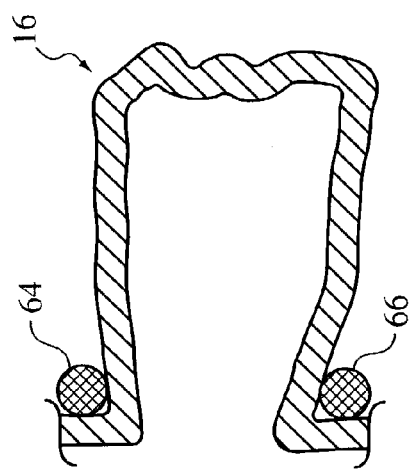
FIGS. 11A-D are schematic representations showing the capture and isolation of the lumen of the LAA by a device equipped with the assembly shown in FIG. 7.

One method of using the assembly 60 to capture, for example, the LAA, is for the surgeon to obtain epicardial access to the heart and locate the pins 64, 66 in perpendicular relation to the appendage 16, as shown, for example, beginning in FIG. 10. The pins 64, 66 could subsequently be deployed to an "open" position (for example as previously shown as position "b" in FIG. 8B through operation of a controller device). Once deployed, the surgeon would continue to operate a controller (as previously described) to rotate the textured pins 64, 66 in a manner that would cause the pins 64, 66 to progress along the surface of the LAA 16 (or for the appendage to be "drawn-in" to the opening between the pins) as shown, for example, in FIGS. 11A-11C. Once the pins 64, 66 have been positioned at the base 36 of the LAA 16 (as show in FIG. 11C), the pins 64, 66 move back towards one another (i.e. lateral planar movement) to close-off the orifice 34 of the LAA 16 as show in FIG. 11D. Once the orifice 34 has been closed, a clamp (not shown) may be deployed about the base 36 of the LAA. Alternately, the pins 64, 66 may be electrodes capable of transmitting a bipolar radio frequency. It is preferable if the energy transmitted is of sufficient amplitude and duration to cause the base of the LAA 36 to form a lesion and thereby fuse the orifice closed to isolate the lumen 32 of the LAA, as shown in FIG. 1I D.

Figure 12A:
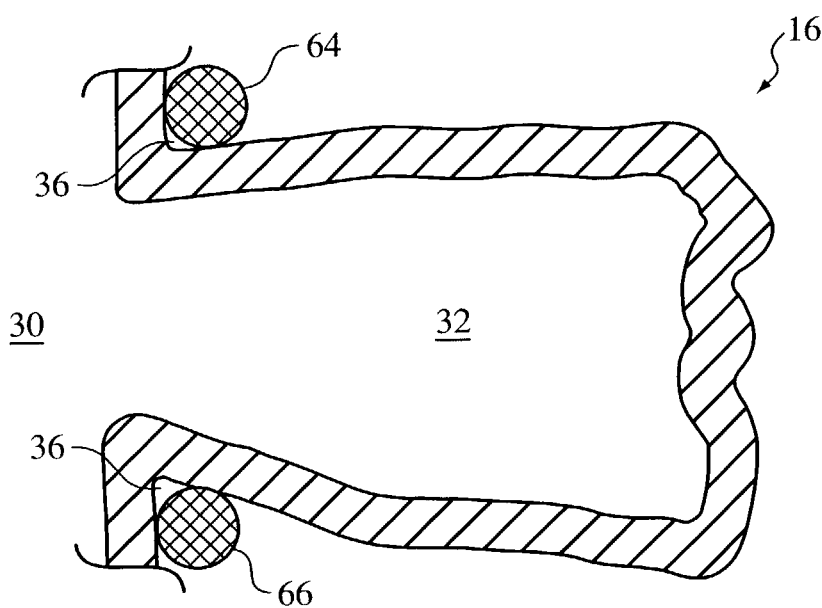
FIGS. 12A-B are schematic cross-sectional representations showing the pins of the device of FIG. 7 fully deployed (A) at the base of the LAA and subsequently clamped (B) thereby isolating the lumen of the LAA from the left atrium.
Figure 13A:
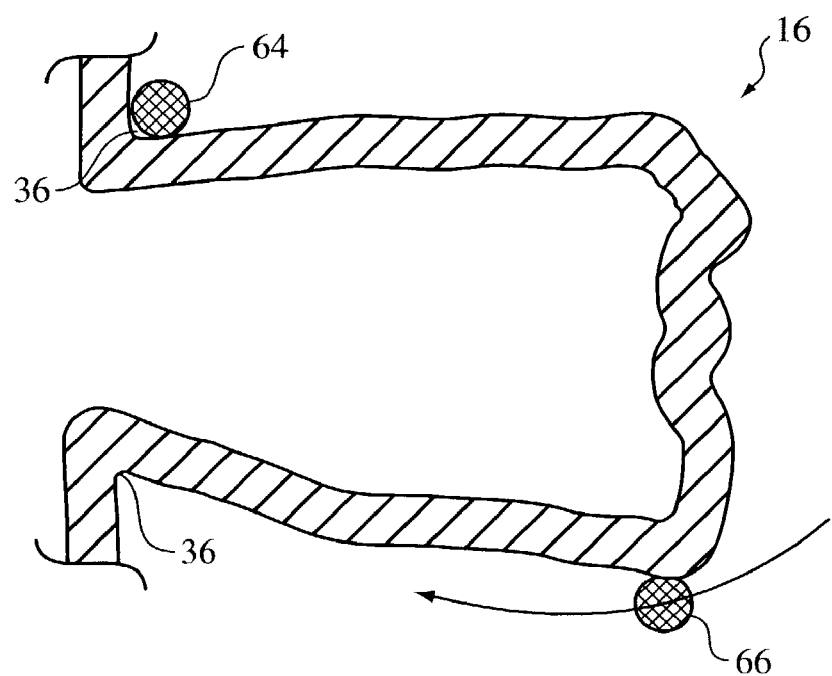
FIGS. 13A-B are schematic cross-sectional representations showing the pins of the device of FIG. 7 fully deployed (A) and being placed adjacent the base of the LAA by one pin sweeping an arc about the other pin, and subsequently clamped (B) thereby isolating the lumen of the LAA from the left atrium.
Figure 13B:
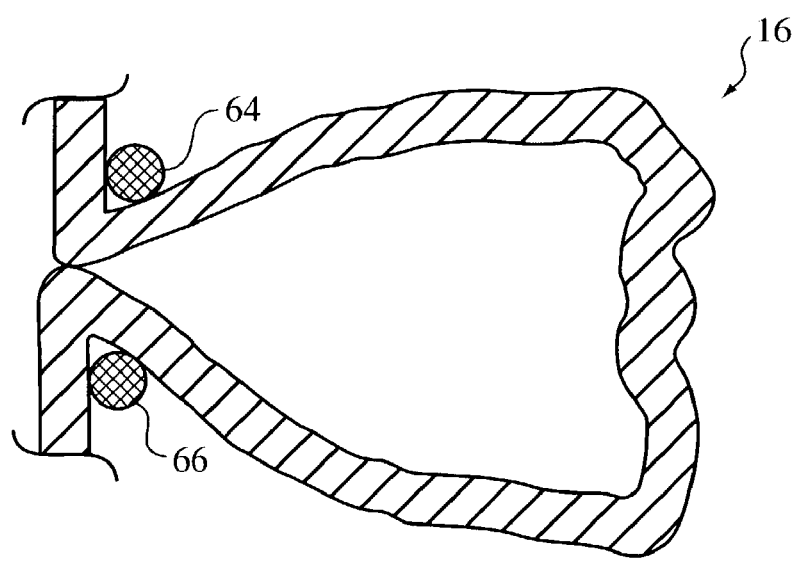

Alternatively, the pins 64, 66 may be "opened" prior to positioning the assembly around the LAA 16. In that case, the surgeon may be able to place the pins 64, 66 directly around the base 36 of the LAA 16, for example, as shown in FIG. 12A. If the pins 64, 66 cannot be placed directly at the base 36 of the LAA 16, it is preferable that the pins 64, 66 are able to sweep an arc relative to one another, as shown for example, in FIGS. 13A and B. FIG. 13A shows placement of a first pin 64 adjacent the base 36 of the LAA while the second pin 66 sweeps an arc toward the opposite side of the LAA 16. FIG. 13B shows the preferable position of pins 64, 66 prior to initiating one of the isolation/exclusion/occlusion methods described herein.

Figure 11D:
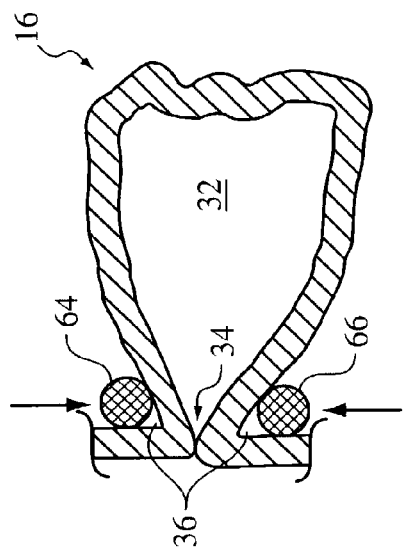
Figure 11A:
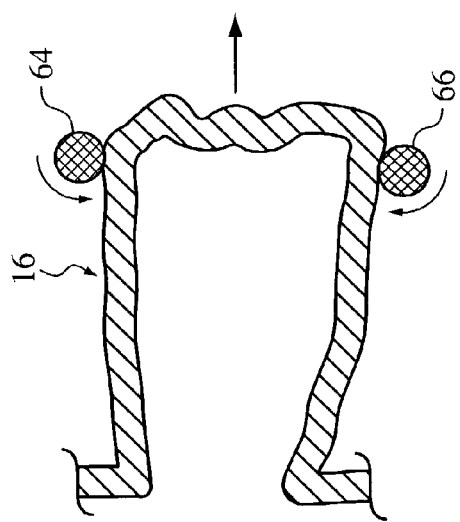
Figure 11B:
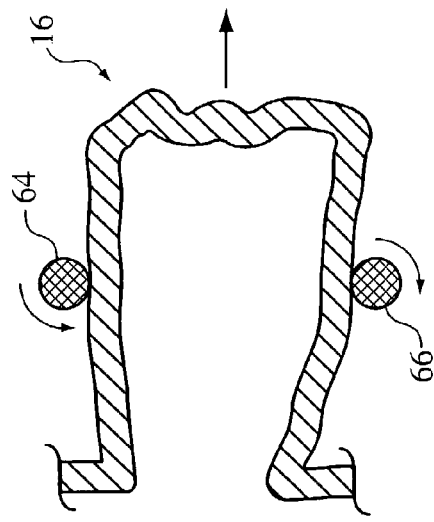
Figure 12B:
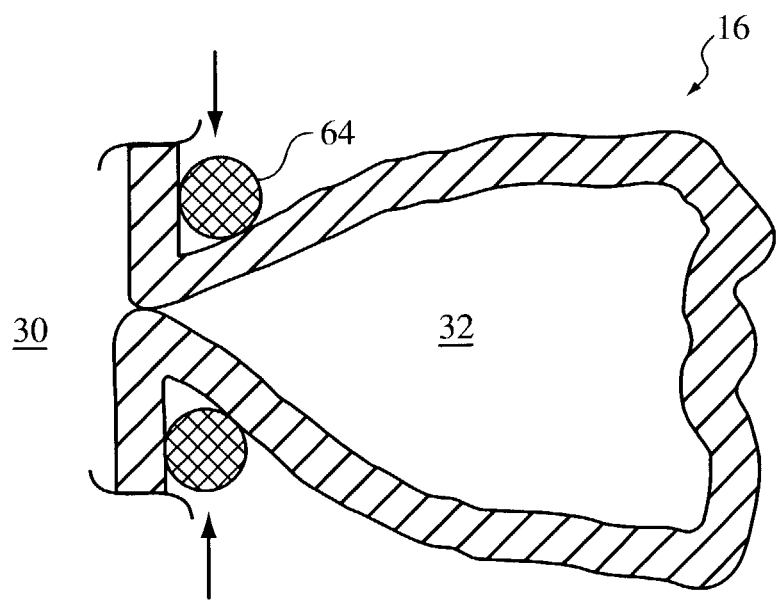

In any alternative, (i.e. position and deploy or deploy and position) once the textured pins are positioned at the base 36 of the LAA, the pins 64, 66 may be drawn together (i.e., changed from position "b" to position "a" as previously shown in FIG. 8B) to thereby close-off fluid communication between the lumen 32 of the LAA 16 and the left atrium 30 as shown in FIGS. 11D and 12B. In addition, thermal, electrical, or mechanical energy may be transmitted from the textured pins to the epicardial tissue to affect electrical isolation of said tissue. Following the mechanical and/or electrical functional isolation of the LAA 16 from the left atrium 30, a clamp may be deployed to maintain the isolation of the lumen 32 from the atrium 30. One alternative is to engage the pins 64, 66 with one another using a simple mechanism such as end caps (not shown) and detach the textured pins 64, 66 from the pin holder, leaving the pins 64, 66 in place to isolate the base 36 of the LAA.

In another preferred embodiment using the devices and methods in accordance with the present invention, following the occlusion of the orifice of the LAA, the appendage remains viable allowing capillary blood flow, and hence hormonal exchange, between the appendage and surrounding tissue. It is most preferable if the lumen of the LAA can be isolated without destroying the vascularization of the tissue of the appendage.

Nothing in the above description of the devices is meant to limit the present invention to any specific materials, geometry, or orientation of elements. Many part/orientation substitutions are contemplated within the scope of the present invention and will be apparent to those skilled in the art. The embodiments described herein are presented by way of example only and should not be used to limit the scope of the invention.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

What is claimed is:

1. An apparatus for selectively isolating a lumen of a left atrial appendage (LAA) from a patient's left atrium of a heart thereby preventing passage of embolic material from said LAA while maintaining physical integrity of said left atrium and said LAA of said heart, the apparatus comprising:
   an extension having a proximal end and a distal end and defining a longitudinal axis;
   means at the distal end of the extension for non-invasively securing the LAA via contact with the exterior surface of the LAA, wherein said securing means is adapted to entirely enclose said LAA;
   means at the distal end of the extension for preventing passage of embolic material from said LAA while maintaining physical integrity of said left atrium and said LAA, wherein said preventing and maintaining means is adapted to disengage from said apparatus and remain securely in place at the base of said LAA; and
   means for cinching said preventing and maintaining means wherein said cinching means is adapted to maintain tension in said preventing and maintaining means thereby isolating the lumen of said LAA, wherein physical integrity of said left atrium and said LAA is maintained and said LAA remains viable during operation of the apparatus, further wherein said preventing and maintaining means and said cinching means are located outside of said securing means during operation of the apparatus including before and during isolation of the LAA.

2. The apparatus of claim 1 wherein the extension comprises a shaft having dimensions suitable for introduction into a patient via an endoscopic access port.

3. The apparatus of claim 2 wherein the shaft is less than 15 mm in diameter.

4. The apparatus of claim 1 wherein the non-invasive securing means comprises a capture chamber.

5. An apparatus for isolating the lumen of the left atrial appendage (LAA) from the left atrium of a patient, the apparatus comprising:
   a capture chamber having an intake port for receiving the LAA, said chamber being of sufficient capacity to enclose the LAA;
   a snare adapted to isolate the LAA, wherein the snare is disposed outside the capture chamber during operation of the apparatus including before and during isolation of the LAA by the snare, wherein physical integrity of said left atrium and said LAA remains viable is maintained and said LAA remains viable during operation of the apparatus;
   a cinch adapted to engage the snare, wherein the cinch is disposed outside the capture chamber during operation of the apparatus including before and during isolation of the LAA by the snare; and an actuator proximal to the capture chamber, wherein said actuator is adapted to actuate the cinch to draw the snare is adapted to disengage from the actuator and remain securely in place at the base of the LAA.

6. The apparatus of claim 5 wherein the capture chamber further includes an aspiration port.

7. The apparatus of claim 6 wherein the aspiration port is located on an opposite axis relative to the intake port.

8. The apparatus of claim 6 wherein the intake port is comprised of a flexible structure that allows the LAA to be non-invasively secured within the capture chamber upon the application of negative pressure to the aspiration port.

9. The apparatus of claim 8 wherein the intake port is substantially circular and has a diameter between 10 mm and 40 mm.

10. The apparatus of claim 5 wherein the capture chamber is oriented in a collapsed state whereby upon deployment to an open state, a sufficient capacity to entirely enclose the LAA is realized.

11. The apparatus of claim 5 wherein said actuator is further adapted to disengage said snare from the actuator.

* * * * *

UNITED STATES PATENT AND TRADEMARK OFFICE
CERTIFICATE OF CORRECTION

PATENT NO. : 7,527,634 B2
APPLICATION NO. : 10/439280
DATED : May 5, 2009
INVENTOR(S) : Zenati et al.

It is certified that error appears in the above-identified patent and that said Letters Patent is hereby corrected as shown below:

Column 12, line 7, delete "FIG." and substitute -- FIGS. -- therefor.

Column 14, Claim 5, line 61, delete "remains viable".

Column 15, Claim 5, line 2, after "snare" insert -- closed at the base of the LAA to isolate the LAA, wherein the snare --.

Signed and Sealed this

Fourth Day of August, 2009

JOHN DOLL
*Acting Director of the United States Patent and Trademark Office*